United States Patent [19]

Evans et al.

[11] Patent Number: 4,770,667
[45] Date of Patent: Sep. 13, 1988

[54] USE OF SUBSTITUTED 2-(2'-HYDROXYARYL)-2H-BENZO-TRIAZOLESULFONATES AS PHOTOSTABILIZING AGENTS FOR NATURAL AND SYNTHETIC FIBRES

[75] Inventors: Neil A. Evans, East Ivanhoe; Ian H. Leaver, Cheltenham; Judi Rosevear, Wantirna South; Peter J. Waters, Gladstone Park; John F. K. Wilshire, Surrey Hills, all of Australia

[73] Assignee: Board of Regents, U T Systems, Austin, Tex.

[21] Appl. No.: 26,737

[22] Filed: Mar. 17, 1987

Related U.S. Application Data

[63] Continuation of Ser. No. 643,963, filed as PCT AU83/00179, Dec. 6, 1983, published as WO84/02365, Jun. 21, 1984, Pat. No. 4,668,235.

[30] Foreign Application Priority Data

Dec. 7, 1982 [AU] Australia .................................... 7151

[51] Int. Cl.$^4$ .......................... C09K 15/30; G03C 1/92; G03C 11/10; D06M 13/30
[52] U.S. Cl. ............................... 8/128.1; 8/115.51; 8/115.7; 8/127.5; 8/115.58; 8/490
[58] Field of Search ................... 8/128 R, 115.58, 490

[56] References Cited

U.S. PATENT DOCUMENTS

| | | | |
|---|---|---|---|
| 3,383,241 | 5/1968 | Davisson et al. | 8/490 |
| 3,849,373 | 11/1974 | Siegle et al. | 525/328.2 |
| 4,001,266 | 1/1977 | Rody et al. | 548/260 |
| 4,141,903 | 2/1979 | Adler | 548/261 |
| 4,219,480 | 8/1980 | White et al. | 548/259 |
| 4,230,867 | 10/1980 | Kintopf et al. | 548/259 |
| 4,668,235 | 5/1987 | Evans et al. | 8/115.58 |

OTHER PUBLICATIONS

Waters, P. J. and N. A. Evans, Textile Research J., 1978, 48, (No. 5), 251–255.

Primary Examiner—A. Lionel Clingman
Attorney, Agent, or Firm—Arnold, White & Durkee

[57] ABSTRACT

A method for protecting synthetic and natural fibres against phototendering. The method comprises treating the fibres with a substituted benzotriazolesulfonate of the following formula:

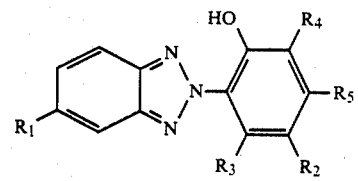

wherein (I) $R_1$ is hydrogen or halogen, $R_2$ is hydrogen or alkyl, $R_3$ is hydrogen or hydroxy, $R_4$ is —SO$_3$X where X is hydrogen or an alkali metal, and $R_5$ is hydrogen, with the proviso that $R_2$ is not methyl when $R_1$ and $R_3$ are hydrogen; or (II) $R_1$, $R_3$ and $R_4$ are hydrogen, $R_2$ is —SO$_3$X where X is hydrogen or an alkali metal, and $R_5$ is —OR$_6$ where $R_6$ is hydrogen or alkyl; or (III) $R_1$ is hydrogen or halogen, $R_2$ is —SO$_3$X where X is hydrogen or an alkali metal, $R_3$ and $R_5$ are hydrogen, and $R_4$ is hydrogen, alkyl or benzyl; or (IV) $R_1$ is —SO$_3$X where X is hydrogen or an alkali metal, $R_2$ is alkyl, $R_3$ and $R_5$ are hydrogen, and $R_4$ is hydrogen or alkyl;

under acidic conditions. The method is particularly suitable for treating wool, silk and nylon fibres, including blends thereof.

16 Claims, No Drawings

USE OF SUBSTITUTED 2-(2'-HYDROXYARYL)-2H-BENZOTRIAZOLESULFONATES AS PHOTOSTABILIZING AGENTS FOR NATURAL AND SYNTHETIC FIBRES

This is a continuation of application Ser. No. 643,963, filed as PCT AU83/00179 on Dec. 6, 1983, published as WO84/02365 on Jun. 21, 1984, now U.S. Pat. No. 4,668,235.

This invention relates to a method for protecting synthetic and natural fibres against phototendering by the use of substituted 2-(2'-hydroxyaryl)-2H-benzotriazolesulfonates.

Phototendering is a light-induced phenomenon which manifests itself as a loss in strength and abrasion resistance of the fibre. The resultant damage is particularly noticeable in woollen car upholstery and in woollen curtains of the scrim variety, which sometimes fall apart within a few years upon exposure to sunlight— even through glass. It is of course well known that synthetic fibres and plastics are also damaged by light and it has become commonplace for additives to be added to the polymeric material before fabrication in the hope of retarding such light-induced damage. Particularly effective additives are certain organic compounds, known as ultraviolet absorbers, which absorb ultraviolet radiation preferentially thereby protecting the fibre or plastic from the damaging effects of sunlight.

The present invention had its origin in the notion that suitably modified ultraviolet absorbers might protect natural protein and synthetic fibres against photodegradation, particularly phototendering. Particularly relevant to the present invention was the observation that certain sulfonic acid derivatives of substituted 2-(2'-hydroxyphenyl)-2H-benzotriazoles, a well-known class of ultraviolet absorber, reduced the rate of photoyellowing of bleached wool [Waters and Evans, Text. Res. J., 48, 251–255, (1978)]. Accordingly, a wide variety of benzotriazolesulfonic acids was synthesized and applied to certain natural and synthetic fibres particularly wool, silk and nylon; their effectiveness in reducing photodegradation is the subject of this invention.

The essential structural feature of 2-(2'-hydroxyphenyl)-2H-benzotriazole photostabilizers is the phenolic hydroxyl group, which is capable of forming both intra- and inter-molecular hydrogen bonds. It is the intramolecurlarly hydrogen-bonded form (Ia) which is responsible for the photoprotective (or photo-stabilizing) effect; if the proportion of the intermolecularly hydrogen-bonded form (Ib) is increased, as can happen in solvents [Heller, Eur. Poly. J., Supplement (1969), 105–132] or polymeric substrates [cf. Leaver, J. Polym. Sci. (Polym. Chem. Ed.) (1982), 20, 2429] capable of disrupting the intramolecular hydrogen bond, then the photostabilizing efficiency is reduced. On the other hand, if the phenolic hydroxyl group is flanked by a bulky substituent (e.g., t-alkyl) located in the ortho position (i.e., at R), then the intramolecular hydrogen bond may be protected to some extent from the disrupting effect of hydrogen bond breaking solvents [see also Heller (reference cited above)]. Particular attention has been paid to this (possibly beneficial) bulky group effect in the research which is the subject of the present application.

There are prior reports of the use of unsulfonated 2-(2'-hydroxyphenyl)-2H-benzotriazoles for the protection, with varying degrees of success, of some natural fibres against light e.g., mohair [van Rensburg, SAWTRI Bull., 12(4), 48–53 (1978)], cotton [van Rensburg, SAWTRI Technical Report No. 309 (1976)] and silk [e.g., Kuwahra, Nakamichi and Shoji, Nippon Sanshigaku Zasshi, 46(6), 486–492 (1977)]. Of particular relevance to the present invention, is the use of sulfonated 2-(2'-hydroxyphenyl)-2H-benzotriazoles for the protection of wool against yellowing [Waters and Evans, Text. Res. J., 48(5), 251–255 (1978); Leaver, Waters and Evans, J. Poly. Sci. (Poly. Chem. Ed.), 17, 1531–1541 (1979)].

The synthesis of substituted sodium 2-(2'-hydroxyphenyl)-2H-benzotriazolesulfonates has been claimed in several recent patents (collected below). However data concerning the specific use of these sulfonates is lacking; in particular, no protection of wool, wool-blends or synthetic fibres against sunlight is disclosed. The following relevant patents are recorded:

| | | | |
|---|---|---|---|
| Japanese Pat. | 7,510,623 | 23 Apr., 1975 | (Toyobo Co Ltd) |
| U.S. Pat. No. | 3,849,373 | 19 Nov., 1974 | (Du Pont de Nemours) |
| Swiss Pat. | 615,165 | 15 Jan., 1980 | (Ciba-Geigy) |
| Swiss Pat. | 615,167 | 15 Jan., 1980 | (Ciba-Geigy) |
| Ger. Pat. | 2,835,846 | 22 Feb., 1979 | (Ciba-Geigy) |
| Ger. Pat. | 2,835,529 | 01 Mar., 1979 | (Ciba-Geigy) |
| U.S. Pat. No. | 4,141,903 | 27 Feb., 1979 | (Ciba-Geigy) |

It is therefore an object of the present invention to provide means to protect synthetic and natural fibres such as wool, silk and nylon from photodegradation. The extension of this invention to dyes fibres is also intended.

According to the present invention there is provided a method for protecting synthetic and natural fibres against photodegradation which comprises treating the fibres with a substituted benzotriazolesulfonate of the following formula:

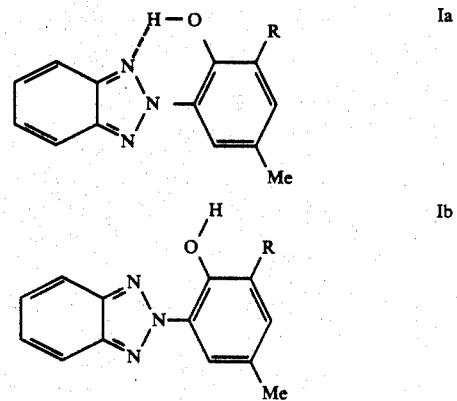

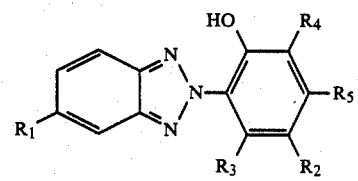

wherein
(I) $R_1$ is hydrogen or halogen, $R_2$ is hydrogen or alkyl, $R_3$ is hydrogen or hydroxy, $R_4$ is $-SO_3X$ where X is hydrogen or an alkali metal, and $R_5$ is hydrogen, with the proviso that $R_2$ is not methyl when $R_1$ and $R_3$ are hydrogen; or (II) $R_1$, $R_3$ and $R_4$ are hydrogen, $R_2$ is $-SO_3X$ where X is hydrogen or an alkali metal, and $R_5$ is $-OR_6$ where $R_6$ is hydrogen or alkyl; or (III) $R_1$ is hydrogen or halogen, $R_2$ is $-SO_3X$ where X is hydrogen or an alkali metal, $R_3$ and $R_5$ are hydrogen, and $R_4$ is hydrogen, alkyl or benzyl; or (IV) $R_1$ is $-SO_3X$ where X is hydrogen or an alkali metal, $R_2$ is alkyl, $R_3$ and $R_5$ are hydrogen, and $R_4$ is hydrogen or alkyl;

under acidic conditions.

Preferred alkyl groups include methyl, ethyl, propyl (n and i), butyl (s and t), t-amyl and t-octyl. Preferred halogen is chlorine and preferred alkali metal is sodium.

Fibres found to be particularly amenable to the process are wool (including dyed wool), silk and nylon fibres, and blends thereof.

Preferred embodiments of the invention will now be described with reference to the following examples which illustrate the extent of photodegradation in wool, silk and nylon samples treated with the benzotriazole-sulfonates according to the invention. The extent of photo-degradation was measured by the breaking load found for fabric strips or yarns before and after irradiation. Unless otherwise stated in the examples, the ultraviolet absorbers (5% o.w.f.) were normally applied to the fabric at 80° for 90 minutes from an aqueous dyebath (liquor:wool ratio=60:1) containing sulfuric acid (3% o.w.f.) and sodium sulfate (5% o.w.f.) using an Ahiba laboratory dyeing machine. Exhaustions (as measured by optical density changes of the dyebaths) ranged from 60-100% (mainly 80-100%).

Treated and control fabric samples (30 cm×25 cm) were exposed for up to 2000 hr at a distance of 20 cm from a mercury-tungsten-phosphor lamp (Philips MBTF or ML 500W type), which is considered to provide irradiation similar to that of sunlight.

Breaking loads were determined in the weft direction on conditioned (20°; 65% r.h.) fabric strips (weft 125 mm and warp 40 mm; rate of extension 125 mm/min). The results quoted are the means of six measurements. The results are collected in eight Examples. Examples 1-7 are concerned with wool [including dyed wool (see Example 9)], and Example 8 with nylon.

EXAMPLE 1
PROTECTION OF WOOL AGAINST LIGHT

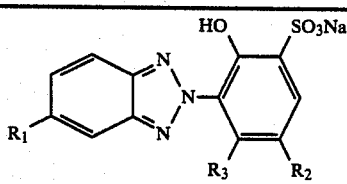

| Substituents | | | Breaking Load (lb) | | Strength (%) remaining after irradiation |
|---|---|---|---|---|---|
| $R_1$ | $R_2$ | $R_3$ | Before | After 2000 hr | |
| Untreated | | | 34.0 | 4.7 | 13.8 |
| H | H | OH | 34.3 | 14.2 | 41.4 |
| H | t-Oct | H | 45.3 | 11.5 | 25.4 |
| H | t-Bu | H | 37.8 | 19.0 | 50.3 |
| Cl | Me | H | 35.6 | 13.4 | 37.6 |

EXAMPLE 2
PROTECTION OF WOOL AGAINST LIGHT

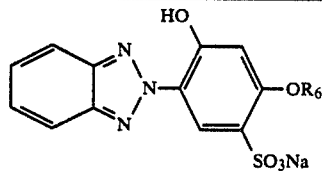

| Substituent $R_6$ | Breaking Load (lb) | | Strength (%) remaining after irradiation |
|---|---|---|---|
| | Before | After 2000 hr | |
| Untreated | 34.0 | 5.0 | 14.7 |
| H | 36.1 | 21.6 | 59.8 |
| Me | 35.9 | 21.8 | 60.7 |
| n-$C_{12}H_{25}$ | 37.2 | 25.1 | 67.5 |

EXAMPLE 3
PROTECTION OF WOOL AGAINST LIGHT

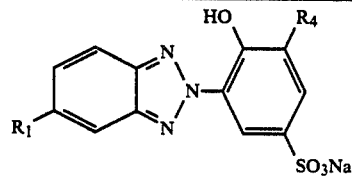

| $R_4$ | $R_1$ | Breaking Load (lb) | | Strength (%) remaining after irradiation |
|---|---|---|---|---|
| | | Before | After 2000 hr | |
| Untreated | | 33.3 | 9.1 | 27.3 |
| H | H | 36.3 | 16.8 | 46.3 |
| Me | H | 43.1 | 22.1 | 51.3 |
| Et | H | 36.1 | 15.1 | 41.8 |
| n-Pr | H | 35.4 | 24.1 | 68.1 |
| i-Pr | H | 33.7 | 24.7 | 73.3 |
| s-Bu | H | 34.9 | 26.4 | 75.6 |
| $CH_2Ph$ | H | 35.1 | 22.8 | 65.0 |
| H | Cl | 36.4 | 12.8 | 35.2 |
| Me | Cl | 35.9 | 16.6 | 46.2 |

EXAMPLE 4
PROTECTION OF WOOL AGAINST LIGHT

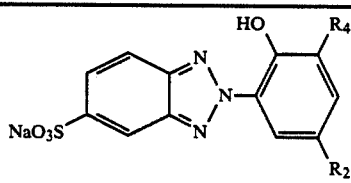

| $R_4$ | $R_2$ | Breaking Load (lb) | | Strength (%) remaining after irradiation |
|---|---|---|---|---|
| | | Before | After 2000 hr | |
| Untreated | | 40.5 | 7.5 | 18.5 |
| H | Me | 41.7 | 21.7 | 52.0 |
| Me | Me | 41.7 | 27.0 | 64.7 |
| i-Pr | t-Bu | 38.0 | 29.8 | 78.4 |
| t-Bu | Me | 41.6 | 35.6 | 85.6 |
| t-Am | Me | 37.6 | 31.8 | 84.6 |

EXAMPLE 5

PROTECTION OF WOOL AGAINST LIGHT: EFFECT OF APPLICATION pH

| Sample | pH+ | % Breaking Load Remaining after 2000 hr |
|---|---|---|
| Untreated Wool | — | 15.1 |
| Control | 2 | 15.5 |
| +Absorber* | 2 | 85.6 |
| Control | 4 | 12.6 |
| +Absorber* | 4 | 68.6 |
| Control | 5.5 | 12.1 |
| +Absorber* | 5.5 | 53.5 |

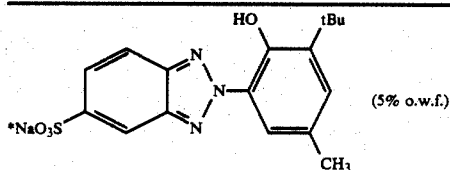

(5% o.w.f.)

+Exhaustion of Absorber Data: pH2 (93%); pH4 (88%); pH5.5 (76%).

EXAMPLE 6

PROTECTION OF WOOL AGAINST LIGHT: EFFECT OF ABSORBER CONCENTRATION

| Absorber* Concentration (% o.w.f.) | % Breaking Load Remaining after 2000 hr |
|---|---|
| 0 | 10.3 |
| 0.6 | 28.9 |
| 1.2 | 44.5 |
| 3.1 | 61.9 |
| 5.0 | 77.4 |

*Applied at pH 2; for Formula, see Example 5.

EXAMPLE 8

PROTECTION OF SILK AND NYLON AGAINST LIGHT

| Fabric | Treatment* | % Breaking Load Remaining |
|---|---|---|
| Silk+ | None | 4 |
|  | Absorber | 28 |
| Nylon 66++ | None | 16 |
|  | Absorber | 67 |

*Absorber (3% o.w.f. used): for Formula, see Example 5
+Irradiated for 500 HR at 45°
++Irradiated for 800 HR at 45°.

EXAMPLE 7

PROTECTION OF DYED WOOL AGAINST LIGHT

| Treatment (or Additive) | After 1000 hr at 45° BL (% RET)* | ΔE<sup>δ</sup> | After 600 hr at 70° BL (% RET)* | ΔE<sup>δ</sup> |
|---|---|---|---|---|
| None | 29.8 | 8.6 | 19.1 | 21.8 |
| Absorber+ | 67.3 | 1.2 | 55.6 | 10.9 |
| Bordeaux Dye++ | 42.3 | 5.9 | 35.5 | 12.4 |
| Bordeaux Dye & Absorber | 60.4 | 4.1 | 50.2 | 6.7 |
| Green Dye++ | 40.5 | 14.3 | 32.3 | 15.6 |
| Green Dye & Absorber | 60.2 | 7.4 | 41.5 | 9.8 |
| Brown Dye++ | 45.8 | 5.2 | 35.7 | 8.6 |
| Brown Dye & Absorber | 67.9 | 2.0 | 52.7 | 4.3 |
| Yellow Dye++ | 41.4 | 10.5 | 30.2 | 11.8 |
| Yellow Dye & Absorber | 57.3 | 5.7 | 51.5 | 6.8 |
| Grey Dye++ | 37.3 | 6.8 | 29.4 | 10.3 |
| Grey Dye & Absorber | 53.1 | 3.9 | 49.8 | 6.2 |

*% Breaking Load Retained
+Absorber (2% o.w.f.) used: for Formula, see Example 5.
++Isolan (Bayer) Dyes used: Premetallized Azo Dyes (Lightfastness ≧ 6) Applied at Standard Depth.
δΔE: Colour Difference Values, based on the CIE L,a,b colour scheme (A measure of dye fading).

The ultraviolet absorbers shown in Examples 1–3 were prepared via direct sulfonation (with chlorosulfonic acid) of the parent benzotriazole derivatives (a typical preparation is described below).

The sulfonates shown in Example 4 where prepared by the reduction (with sodium dithionite) of the corresponding sodium o-nitrophenylazobenzenesulfonates (a typical preparation is described below).

In the first four examples, the first two columns of data show the breaking loads before and after irradiation; the third column shows the percentage strength remaining in the fabric after irradiation (this parameter was derived directly from the data shown in the first two columns). An assessment of the data collected in the examples leads to the following general conclusions:

(i) All the sodium benzotriazolesulfonates studied protect wool against photodegradation. The degree of protection afforded increases as the percentage of sulfonate o.w.f. is increased (see Examples 6).

(ii) The location of the sulfonic acid group in the molecule affects the degree of protection, protection being less when the sulfonic acid group is adjacent to the hydrogen bonded phenolic group (see Example 1) than when it is located elsewhere (see Examples 2–4).

(iii) The pH at which the benzotriazolesulfonate is applied has an effect on its subsequent protective affect (see Example 5).

(iv) Incorporation of a long chain alkyl group into the molecule increases the degree of photoprotection (see Example 2).

(v) Incorporation of a bulky alkyl or aralkyl group (specifically t-Bu, i-Pr, s-Bu, t-Am or benzyl) into the molecule ortho to the hydrogen bonded OH group increases dramatically the degree of protection obtained (see Examples 3 and 4). This result confirms the original hypothesis that such ortho-located bulky groups would have a beneficial effect on the degree of protection afforded by 2-(2'-hydroxyaryl)-2H-benzotriazolesulfonates.

(vi) The invention is particularly useful for dyed wool (see Example 7), the dyes [Isolans (Bayer)] being premetallised azo dyes of the sort frequently used in car upholstery. It will be seen that dyed fabrics treated with a t-butyl-benzotriazolesulfonate are protected not only against phototendering (B.L. column) but also, to some extent, against dye photofading (ΔE column). In addition to irradiation at 45° (for 1000 h), comparisons were also made for irradiations at 70° C. (for 600 hr), conditions under which the fabric temperature exceeds 80° C. Such a temperature is likely to be experienced by the sunlight-irradiated upholstery fabric of a car during a warm summer's day.

(vii) A further study (see Example 8) showed that both silk (absorber applied at pH 2) and delustred nylon 66 (absorber applied at pH 4) were protected against phototendering by the t-butyl-benzotriazolesulfonate.

PREPARATION OF SODIUM 2-(2'-HYDROXYARYL)-2H-BENZOTRIAZOLE-SULFONATES (i)

Preparation of sodium 3-(2'H-benzotriazol-2'-yl)-5-t-butyl-2-hydroxybenzenesulfonate

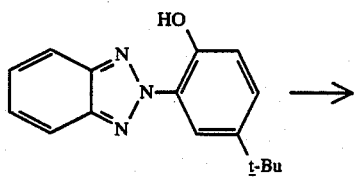

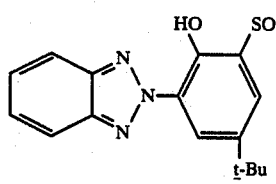

This procedure was used for all the sulfonates shown in Examples 1–3. When chlorosulfonic acid (2.20 g; 19 mmol) was added dropwise to a warm (60°) stirred solution of 2-(2'H-benzotriazol-2'-yl)-4-t-butylphenol (5.0 g; 19 mmol) in chlorobenzene (50 ml), a precipitate (the starting benzotriazole) was formed. However, when the temperature of the mixture was raised to the boiling point, this precipitate dissolved and, after about 10 min, a fresh precipitate (the sulfonic acid) was formed. After boiling under reflux for 2 hr, the mixture was cooled, and the precipitate filtered and washed several times with hexane. This solid was dissolved in water and the solution filtered to remove some amorphous material. The filtrate was then brought to pH 7 by the addition of 10% sodium carbonate solution, and the resultant precipitate (the title sodium salt) (3.08 g) filtered, washed with ice-cold water and dried. Recrystallization from boiling water gave colourless needles. $^1$H n.m.r. (dimethyl sulfoxide-d$_6$): δ1.33, s, t-Bu; 7.65, d(Jc. 2 Hz), H4 or H6; 7.80, d(Jc. 2 Hz), H6 or H4; 11.03, s, OH. The benzotriazole ring protons were revealed as an AA'BB' pattern centred at δ7.80. The product absorbed in water at 297 and 330 nm.

(ii)

Preparation of sodium 2-(3'-t-amyl-2'-hydroxy-5'-methyl)phenyl-5-(2H)-benzotriazolesulfonate

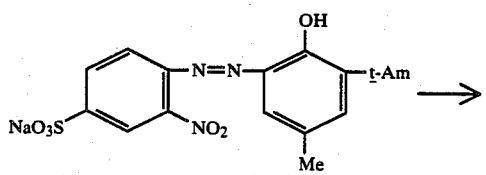

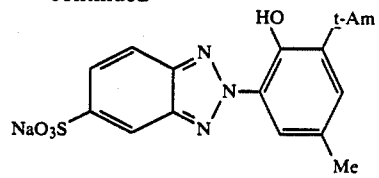

This procedure was used for the sulfonates shown in Example 4. The starting dye was prepared by coupling 4-amino-3-nitrobenzene-sulfonic acid with 2-t-amyl-4-methylphenol under acidic conditions [cf. Rody et al (Ciba-Geigy), Ger. Pat. No. 2,334,770 (14 Mar. 1974); Rosevear and Wilshire, Aust. J. Chem., 35, 2089, 1982]. The resultant dye was isolated by bringing the pH of the mixture to 7 with 1N hydrochloric acid and then adding salt. Some residual stickiness (due to the presence of unreacted phenol) was removed by suspending the dye in boiling hexane for 15 min. To a stirred hot (steam bath) solution of the dye (2.78 g; c. 7 mmol) in 4N sodium hydroxide (24 ml) was added dropwise a solution of sodium dithionite (not less than 85% pure) (6.3 g; 28 mmol) in water (24 ml). The initial deep purple colour of the solution was slowly replaced by an orange-yellow colour. After 3 hr on the steam bath, the solution was filtered hot and the title sodium salt (1.38 g) crystallized from the filtrate as pale yellow crystals. $^1$H n.m.r. (dimethyl sulfoxide-d$_6$): δ0.67, t(Jc. 7 Hz), CH$_2$CH$_3$ 1.42, s, C(CH$_3$)$_2$; 1.97, q(Jc. 7 Hz), CH$_2$CH$_3$; 2.37, s, ArCH$_3$; 7.17, d(Jc. 2 Hz), H4'; 7.90, d(Jc. 2 Hz), H6'; 11.20, vb, OH. The remaining signals could not be assigned. The product absorbed in water at 305 and 348 (inflexion) nm.

We claim:

1. A method for protecting fibres against phototendering which comprises treating the fibres under acidic conditions with a substituted benzotriazolesulfonate of the following formula:

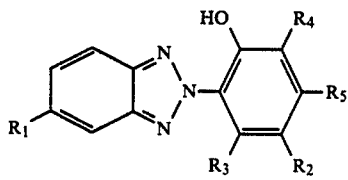

wherein R$_1$ is hydrogen or halogen, R$_2$ is —SO$_3$X where X is hydrogen or an alkali metal, R$_3$ and R$_5$ are hydrogen, and R$_4$ is alkyl or benzyl.

2. A method as defined in claim 1, wherein said acidic conditions involve adjustment to a pH within the range of 2.0–5.5 with sulphuric acid.

3. A method as defined in claim 1, in which the fibre is treated for about 90 minutes at about 80° C.

4. A method as defined in claim 2, in which the fibre is treated for about 90 minutes at about 80° C.

5. A method as defined in any one of claims 1–4, in which the substituted benzotriazolenesulfonate is in an aqueous liquor and the liquor and fibre are in a ratio of about 60:1.

6. A method as defined in any one of claims 1–4, in which the fibre is wool, including dyed wool, silk, nylon or blends thereof.

7. A method as defined in any one of claims 1–4, in which, in the formula of the substituted benzotriazolesulfonate, the halogen is chlorine, the alkali metal is sodium, and the alkyl is methyl, ethyl, propyl (n and i), butyl (s and t), or t-amyl.

8. A method as defined in claim 1, in which, in the formula of the substituted benzotriazolesulfonate: $R_1$ is hydrogen, X is sodium, and $R_4$ is n-propyl, i-propyl, s-butyl or benzyl.

9. A method as defined in claim 1, in which, in the formula of the substituted benzotriazolesulfonate: $R_1$ is hydrogen, X is sodium and $R_4$ is i-propyl.

10. A method as defined in claim 1, in which, in the formula of the substituted benzotriazolesulfonate: $R_1$ is hydrogen; $R_4$ is methyl, ethyl, propyl (n or i); butyl (s or t) or t-amyl.

11. The method of claim 10 wherein $R_4$ is t-butyl.

12. A fibre which has been treated against phototendering with an agent which comprises a substituted benzotriazolesulfonate of the following formula:

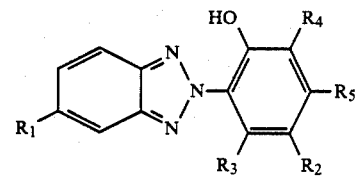

wherein $R_1$ is hydrogen or halogen $R_2$ is —$SO_3X$ where X is hydrogen or an alkali metal, $R_3$ and $R_5$ are hydrogen, and $R_4$ is alkyl or benzyl; under acidic conditions.

13. The fibre of claim 12 wherein $R_1$ is hydrogen; $R_4$ is methyl, ethyl, propyl (n or i), butyl (s or t) or t-amyl.

14. The fibre of claim 13 wherein $R_4$ is t-butyl.

15. The method of claim 1 wherein the fibre is a natural fibre.

16. The method of claim 1 wherein the fibre is a synthetic fibre.

* * * * *

UNITED STATES PATENT AND TRADEMARK OFFICE
CERTIFICATE OF CORRECTION

PATENT NO. : 4,770,667
DATED : September 13, 1988
INVENTOR(S) : Neil A. Evans, et al.

It is certified that error appears in the above—identified patent and that said Letters Patent is hereby corrected as shown below:

On the title page of the patent, delete the incorrect Assignee "Board of Regents, U T Systems, Austin, Tex." and substitute the actual Assignee:

--

Commonwealth Scientific and
Industrial Research Organization,
Australian Capital Territory,
Australia --

Signed and Sealed this

Twentieth Day of June, 1989

Attest:

DONALD J. QUIGG

Attesting Officer

Commissioner of Patents and Trademarks